United States Patent [19]

Osada et al.

[11] Patent Number: 4,898,727
[45] Date of Patent: Feb. 6, 1990

[54] DEODORANT AND FILTER USING SAME, AS WELL AS METHOD OF PRODUCING THE DEODORANT

[75] Inventors: Koji Osada, Yawata; Haruyuki Date, Sakai; Yasuhiro Saihara, Kadoma; Toshiyuki Yamauchi, Ibaragi; Shiro Koike, Shijonawate, all of Japan

[73] Assignee: Matsushita Electric Works, Ltd., Osaka, Japan

[21] Appl. No.: 878,324

[22] Filed: Jun. 25, 1986

[30] Foreign Application Priority Data

Oct. 15, 1985 [JP]  Japan .............................. 60-230424

[51] Int. Cl.[4] ........................... A61L 9/01; C07H 1/08
[52] U.S. Cl. ................................. 424/76.1; 424/76.3; 424/195.1; 422/5; 514/783; 536/128
[58] Field of Search .................. 424/76.1, 76.9, 76.3, 424/195.1; 514/783; 512/5; 260/705; 536/128; 422/5; 239/54, 60

[56] References Cited

U.S. PATENT DOCUMENTS

| | | | |
|---|---|---|---|
| 4,167,559 | 9/1979 | Michel | 424/58 |
| 4,170,638 | 10/1979 | Owades | 424/65 |
| 4,251,508 | 2/1981 | Monsod, Jr. | 424/76.6 |
| 4,681,757 | 7/1987 | Mimasu et al. | 514/783 X |

FOREIGN PATENT DOCUMENTS

| | | | |
|---|---|---|---|
| 53-66434 | 6/1978 | Japan . | |
| 56-100060 | 8/1981 | Japan . | |
| 119951 | 6/1985 | Japan | 424/76.9 |
| 8054 | 1/1986 | Japan . | |
| 94659 | 5/1986 | Japan | 424/76.9 |
| 94660 | 5/1986 | Japan | 424/76.9 |
| 103447 | 5/1986 | Japan | 424/76.9 |
| 119268 | 6/1986 | Japan | 424/76.9 |
| 206448 | 9/1986 | Japan | 424/76.9 |
| 206449 | 9/1986 | Japan | 424/76.9 |
| 209167 | 4/1987 | Japan | 422/5 |
| 5754 | 1/1988 | Japan | 422/5 |

Primary Examiner—Ellis P. Robinson
Assistant Examiner—Susan S. Rucker
Attorney, Agent, or Firm—Burns, Doane, Swecker & Mathis

[57] ABSTRACT

A deodorant consisting of deodorizing ingredients respectively extracted from plants selected from the group consisting of Osmanthus, Forsythia, Paulownia, Syringa, Diospyros, Quercus, Fartugium, Petasites, Pinus, Tsuga, Ginko, Nandina, Loropetalum, Houttuynia, and Oxalis and capable of performing deodorization with respect to a relatively wide range of odors, and performing as a whole the deodorization over a relatively wide range covering one or both sulfur and nitrogen compound odors.

12 Claims, 3 Drawing Sheets

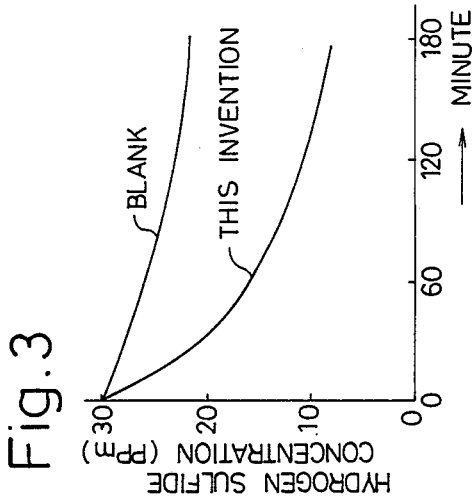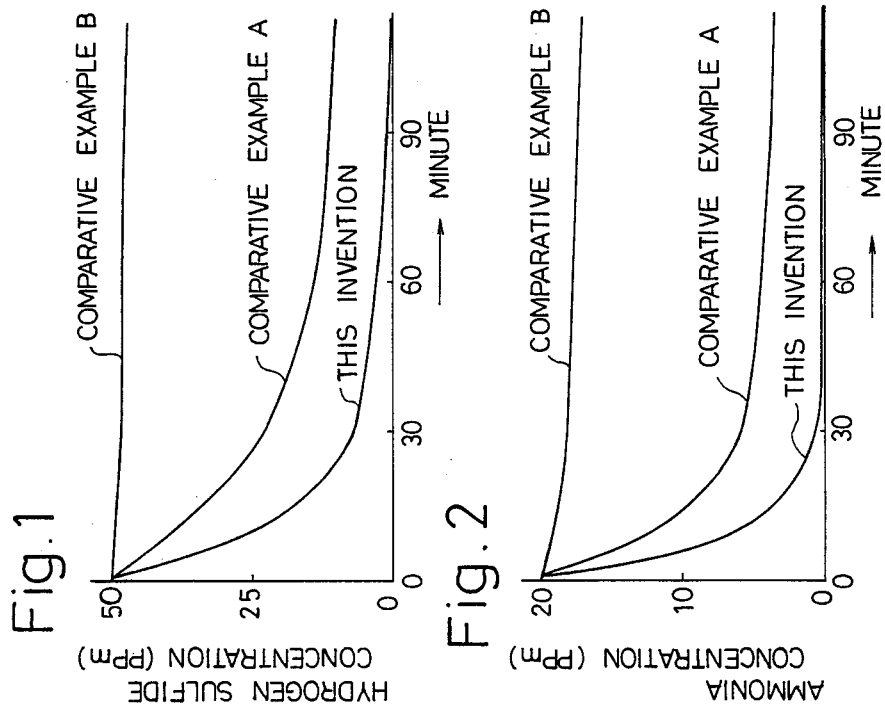

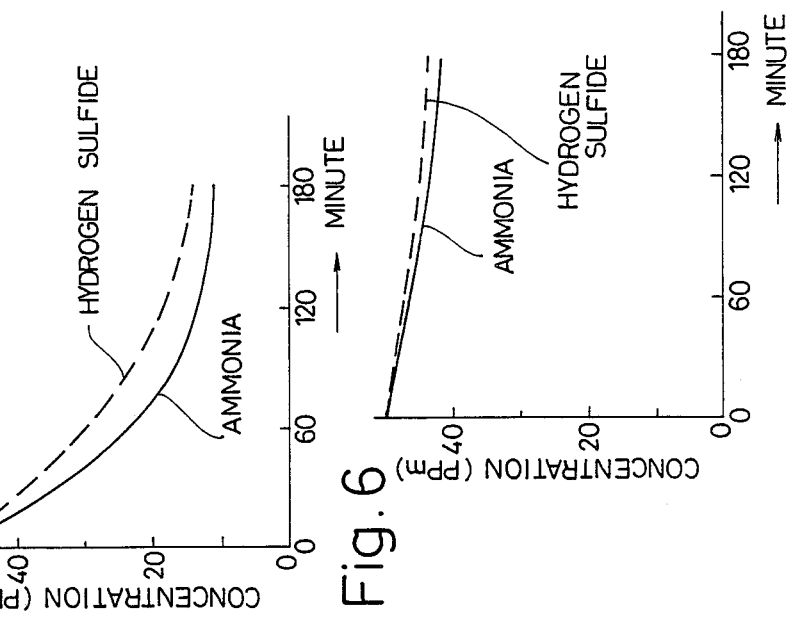
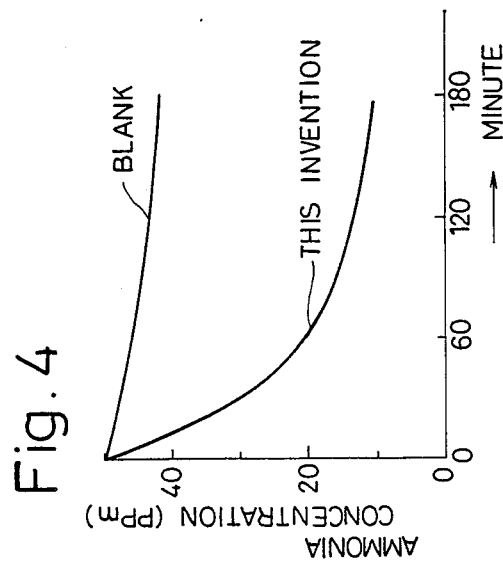
Fig. 4
Fig. 5
Fig. 6

DEODORANT AND FILTER USING SAME, AS WELL AS METHOD OF PRODUCING THE DEODORANT

TECHNICAL BACKGROUND OF THE INVENTION

This invention relates to deodorants, filters using the deodorants, and method of producing the deodorants, and, more specifically, to a deodorant that contains an effective deodorization ingredient to perform deodorizing action on each of such objective odors as sulfur compound, nitrogen compound and the like odors not collectively but individually, a filter employing such deodorant and a method of producing the particular deodorant.

The deodorant of the type referred to is contributive effectively to reduction of bad or foreign odor yielded from factory fume and waste, cigarette smoke, raw sewage, kitchen garbage or the like.

DISCLOSURE OF PRIOR ART

There have been so far proposed various methods of reducing bad or foreign odor. One of such methods uses a perfume substance as a deodorant for the purpose of masking human smell sense from bad or foreign odor with use of the fragrance of the substance. However, this method has such a problem that the fragrant substance has a limit of ability to reduce bad odor, in particular, to cope with strong odor. Further, balancing between fragrance and malodor is very difficult. In addition, the method has another problem that it is hard to achieve a general-purpose deodorizing action, since like and dislike of fragrance vary from person to person. There has been suggested another method by means of ventilating such a space as a room or diffusing the space air, but such method has been defective in that the method must resort to an expensive apparatus and also the ventilation causes room temperature changed.

There is also a method for deodorization by means of chemical reaction to the bad or foreign odor ingredient, but this method required selection of one of different chemical substances as the deodorizing agent with respect to each of different bad or foreign odor ingredients in order to cause the effective chemical reaction thereto, which undesirably results in that the selection work becomes complicated while various sorts of deodorants must be prepared, lowering application flexibility. With respect to the bad odor resulting from decomposition and the like, methods have been suggested for killing bacteria causing the decomposition to stop it and to prevent the bad odor, but they involve problems that expensive bactericidal apparatus is required and it takes time until its effect appears.

Meanwhile, there has been proposed in Japanese Patent Appln. Laid-Open Publication No. 53-66434 by J. Kawachi et al a deodorant which requires no expensive installation nor apparatus, and this deodorant uses active deodorization ingredients obtained from plants and, more specifically, contains extracts thermally extracted from raw or dried leaves of Camellia or Cinnamomum Camphor plant with use of organic solvent and/or water. This invention is advantageous in that the use of the active deodorization ingredients in plants results in simple and low cost production of the deodorant because of easy availability of the plant, but is disadvantageous in that the deodorizing action on the nitrogen or sulfur compound odor is insufficient.

Prior art using the active deodorization ingredients in plants also includes, in addition to Kawachi et al, Japanese Patent Appln. Laid-Open Publication No. 56-100060 by K. Torii et al., and U.S. Pat. Nos. 4,167,559, 4,170,638 and 4,251,508 by G. M. Michel, J. L. Owades and G. G. Monsod Jr., respectively. However, these deodorants have all a relatively narrow range of odor to deal with and are poor in the application flexibility.

TECHNICAL FIELD OF THE INVENTION

A primary object of the present invention is, therefore, to provide a deodorant which contains ingredients extracted from plants and can destroy a relatively wide range of unpleasant odor, to be rich in the application flexibility.

Another object of the present invention is to provide a deodorant which contains one or more deodorizing ingredients extracted from plants and can exhibit excellent deodorizing property, in particular, with respect to sulfur and/or nitrogen compound odors.

A further object of the present invention is to provide a filter which can be incorporated in air cleaners or the like, the filter being impregnated with deodorizing ingredients extracted from plants and particularly effective in deodorizing the sulfur or nitrogen compound odor.

Still another object of the present invention is to provide a filter assembly which can be incorporated in air cleaners or the like, which comprises a combination of filter elements impregnated with respectively different deodorizing ingredients extracted from plants, and is effective in particular in deodorizing the sulfur and nitrogen compound odors.

Yet a further object of the present invention is to provide a method of producing a deodorant containing deodorizing ingredients extracted from plants with use of hydrophilic organic solvent and/or water, which deodorant can destroy a relatively wide range of unpleasant odor with a rich application flexibility.

Other objects and advantages of the present invention shall be made clear in the following description of the invention detailed with reference to preferred examples shown in accompanying drawings.

BRIEF EXPLANATION OF THE DRAWINGS

FIG. 1 is a graph showing variations in hydrogen sulfide concentration with time due to deodorants of the present invention and of comparative Examples A and B;

FIG. 2 is a graph showing variations in ammonia concentration with time due to the deodorants of the present invention and the Comparative Examples A and B;

FIG. 3 is a graph showing variations in hydrogen sulfide concentration with time due to a deodorizing filter of the present invention and a blank;

FIG. 4 is a graph showing variations in ammonia concentration with time due to the deodorizing filter of the present invention and the blank;

FIG. 5 is a graph showing variations in both of hydrogen sulfide and ammonia concentrations with time due to the filter assembly of the present invention;

FIG. 6 is a graph showing variations in both of the hydrogen sulfide and ammonia concentrations with time due to a blank corresponding to the filter assembly of the present invention;

Figure 7:
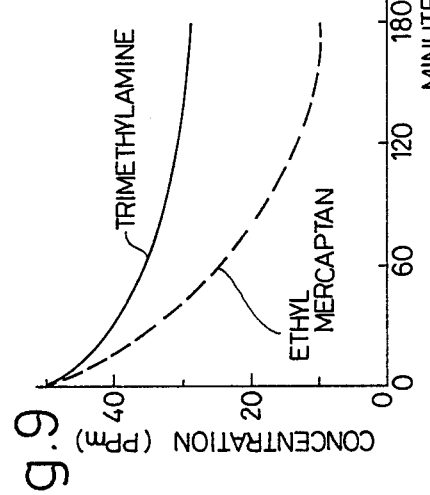
FIG. 7 is a graph showing variations in both the hydrogen sulfide and ammonia concentrations with time due to a comparative example corresponding to the filter assembly of the present invention.

While the present invention shall now be discribed with reference to the preferred examples disclosed, it should be understood that the intention is not to limit the invention only to the particular examples disclosed but rather to cover all alterations, modifications and equivalent arrangements possible within the scope of appended claims.

DISCLOSURE OF PREFERRED EXAMPLES

A deodorant according to the present invention contains deodorizing ingredients extracted from plants. In this case, for sulfur compound odor, the deodorizing ingredients are extracted from Osmanthus plant especially *Osmanthus Fragans, Osmanthus Clicifolius* or *Osmanthus Fortneiu; Forsythia* especially *Forsythia Viridissima* or *Forsythia Suspensa*; Paulownia especially *Paulownia Tomentosa* or *Paulownia Fortunei Hemsley*; Syringa especially *Syringa Vulgaris*; Diospyros especially *Diospyros Kaki*; Quercus especially *Quercus Serrata*; Ligularia especially *Ligularia tussilaginea* or Petasites especially *Petasites japonicus*. For nitrogen compound odor, on the other hand, the deodorizing ingredients are extracted from Pinus plant especially *Pinus Thunbergii, Pinus Pensiflora* or *Pinus Pentaphylla*; Tsuga especially *Tsuga Sieboldii*; Ginkgo especially *Ginkgo Biloba*; Nandina especially *Nandina Domestica*; Loropetalum especially *Loropetalum Chinense*; Houttuynia especially *Houttuynia Cordata*; or Oxalis especially *Oxalis Corniculata* or *Oxalis Martiana*.

Extraction of the deodorizing ingredients from these plants may be conducted in various manners. For example, dried leaves of objective plant are added to any one of hydrophilic organic solvents of such alcohols as ethanol and methanol, such ketones as methyl-ethyl-ketone and acetone or water, or a mixture thereof, and then the mixture is put in a Soxhlet extractor for thermal extraction. The extracted deodorizing ingredients are used individually or in combination with one or ones of deodorizing ingredients of the same group for the objective odor. If necessary, prior to the thermal extraction, the material plant leaves may be put in such hydrophobic organic solvent as hexane or petroleum ether solvent so that the deodorizing ingredients are dissolved out o the plant leaves and are thereafter thermally extracted.

After the extraction of the deodorizing ingredients from the plants, the pH of the extraction liquid is adjusted to fall within a predetermined range to enhance the deodorizing action. That is, for sulfur compound odor, such an alkaline solution as a sodium hydroxide solution is added to the extraction liquid to adjust the pH of the mixture to fall in a range of 7 to 10 to vary from neutral to be weak basic. For nitrogen compound odor, on the other hand, such an acid as citric acid is added to the extraction liquid to adjust the pH to be in a range of 3 to 6 to vary from acidic to weak acidic.

The pH-adjusted deodorizing ingredients are then fixed to a suitable carrier which may be of such a porous organic material as active charcoal, porous mineral as zeolite, porous clay mineral as montmorillonite, inorganic material as silica gel, or the like. The deodorizing ingredient may also be fixedly impregnated in a sheet member of a paper, woven or non-woven cloth, felt, polyurethane foam or the like, or the porous organic or inorganic member carrying the fixed deodorizing ingredients may be adhered with an adhesive onto the carrier of the sheet member. Further, the carrier may be of agar-agar, gelatine or other like material of a gel state at normal temperature, to which the extracted deodorizing ingredient liquid is added to form a jellylike deodorant. In this case, according to a remarkable feature of the present invention, the separately extracted deodorizing ingredients for each of the objective odors are made to be held separately by the carrier, i.e., separately for each of the sulfur and nitrogen compound odors.

Thus obtained carriers are made into the form of a filter which is applicable to the air cleaner or the like, and two or more of such filters respectively holding different deodorizing ingredients for different objective odors are combined to form a filter assembly. Therefore, when an air flow is passed through the filter assembly, the sulfur and nitrogen compound odors can be removed at the same time. It will be appreciated that a deodorizing ingredient effective to such an acid odor as a butyric acid odor or an acetic acid odor and extracted from Paulownia plant, for example, *Paulownia Tomentosa*, or from Houttuynia plant, for example, *Houttuynia Cordata*, may be employed as held in a filter to form one constituent element of the filter assembly.

In impregnating the carrier with the deodorizing ingredients extracted from the plants, an addition of glycerine can provide a moisture retention effect, an addition of a surface-active agent can provide a uniform impregnating effect, and further an addition of such an adhesive of polyvinyl acetate resin, acrylic resin or the like can improve the fixing action of the ingredients to the carrier. When two or more filters respectively holding the different deodorizing ingredients for different objective odors are combined to form the filter assembly, the filters of the sheet or solid carriers respectively retaining the different deodorizing ingredients can be stacked into multiple layers, and such carriers of a relatively high fluidity, as the jellylike carriers may be put respectively in each of proper containers and combined into an assembly. It will be further seen that, when it is desirable to employ the jellylike deodorant which containing the deodorizing ingredients, a pigment may be added to agar-agar, gelatine or the like to provide a desired coloring for an excellent appearance in the resultant product. It is desirable that the deodorant according to the present invention has a deodorizing ingredient concentration of about 0.01 to 1%.

EXAMPLE 1

Leaves of *Osmanthus Fortuneiu* was subjected to hot-water extraction at a temperature of 50° C. and an extract composition was adjusted to be a 0.5 weight % water solution for use as a sulfur compound deodorizing liquid SA. On the other hand, leaves of *Pinus Thunbergii* were subjected to hot-water extraction at 50° C. and the extract composition was adjusted to be a 0.5 weight % solution for use as a nitrogen compound deodorizing liquid NA. Sodium hydroxide was added to the sulfur compound deodorizing liquid SA so that the added liquid had a pH level of 8.0, whereas citric acid was added to the nitrogen compound deodorizing liquid NA so that the added liquid had a pH level of 4.0. 2% of agar-agar was added to the respective pH-adjusted liquids and heated at 100° C. to melt agar-agar. Then a container of 5×10×8 cm was partitioned at its middle and the deodorizing liquids SA and NA containing the melted agar-agar were poured into the partitioned spaces and cooled to set, and jellylike deodorants were obtained.

COMPARATIVE EXAMPLE 1

For comparison with the above Example 1 of the present invention, the sulfur and nitrogen compound liquids SA and NA obtained from the same plants in the same manner as in the Example 1 were mixed in the same quantity without being subjected to the pH adjustment. 2% of agar-agar was added to the mixture, heated at 100° C., poured into a container of the same dimensions as in the Example 1, cooled to set, and a jellylike sample A was obtained. The sample A had a pH level of 5.3.

COMPARATIVE EXAMPLE 2

2% of agar-agar was added to the water solution not containing the foregoing deodorizing liquids SA and NA, heated at 100° C., poured into a container of the same dimensions as in the Example 1, cooled to set, and another comparative sample B was obtained.

The deodorants of Example 1 and the comparative samples A and B were placed respectively in a box having a capacity of 10 liters, and hydrogen sulfide and ammonia gases having initial concentrations of 5 and 20 ppm respectively were flowed into the box. These odor gases were measured with time and resultant measurements were as shown in FIGS. 1 and 2.

Further, the deodorants of Example 1 and the comparative samples A and B were placed respectively in the box having a capacity of 10 liters, a methyl mercaptan gas having an initial concentration of 1 ppm was flowed into the box, and the box was left to stand for one hour. Subsequently, six panelists estimated the gas odor with odor intensities of 6 levels divided as shown in Table I below for convenience sake and the estimation results were given in Table II below.

TABLE I

| Odor levels | Estimation |
|---|---|
| 0 | Odorless |
| 1 | Highly subtly odorous |
| 2 | Subtly Odorous |
| 3 | Easily perceptibly odorous |
| 4 | Strongly odorous |
| 5 | Highly strongly odorous |

TABLE II

| Panelists | A | B | C | D | E | F | Average |
|---|---|---|---|---|---|---|---|
| Example 1 | 0 | 0 | 1 | 1 | 0 | 1 | 0.5 |
| Sample A | 1 | 0 | 2 | 2 | 1 | 1 | 1.2 |
| Sample B | 5 | 4 | 5 | 5 | 5 | 5 | 4.8 |

The similar estimation to that of the above methyl mercaptan was conducted with respect to trimethylamine gas having an initial concentration of 10 ppm and the estimation results were given in Table III below.

TABLE III

| Panelists | A | B | C | D | E | F | Average |
|---|---|---|---|---|---|---|---|
| Example 1 | 0 | 0 | 0 | 1 | 0 | 0 | 0.2 |
| Sample A | 1 | 0 | 2 | 1 | 0 | 0 | 0.7 |
| Sample B | 5 | 4 | 4 | 5 | 4 | 4 | 4.3 |

It will be understood from FIGS. 1 and 2 and Tables II and III that the deodorants of Example 1 according to the present invention have a very high deodorizing effect.

It has been found that, when the deodorant of the present invention was placed in a storehouse of constant temperature and humidity containing rotten vegetable and 24 hours later the odor within the storehouse was checked after 24 hours, the deodorization of the interior of the storehouse has been achieved to a substantial extent.

EXAMPLE 2

Leaves of *Forsythia Viridissima, Diospyros Kaki; Tsuga Sieboldii, Ginkgo Biloba, Nandina Domestica* and *Loropetalum Chinense* were respectively subjected to hot-water extraction at 50° C. the extracted ingredients were adjusted to be 1.0 weight %, and six different deodorizing liquids were obtained. Six groups of silica gel particles of a diameter in average of 1 mm were impregnated respectively with each of these deodorizing liquids in an impregnating amount of each deodorizing liquid of 1 g per 1 g of silica gel as the carrier. The six groups of silica gel particles thus impregnated with the different deodorizing liquids were heated at 50° C. for 24 hours and dried, to obtain silica-gel deodorants containing the deodorizing ingredients extracted from *Forsythia Viridissima* and *Diospyros Kaki* effective with respect to sulfur compound odor and further silica-gel deodorants containing the deodorizing ingredients extracted from *Tsuga Sieboldii, Ginkgo Biloba; Nandina Domestica* and *Loropetalum Chinense* effective with respect to nitrogen compound odor.

COMPARATIVE EXAMPLE 3

A deodorant consisting only of silica gel containing no such deodorizing liquids as used in the Example 2 was used as a blank.

50 g of each of two sorts of the above deodorants of Example 2 containing the deodorizing ingredients effective to the sulfur compound odor and extracted from *Forsythia Viridissima* and *Diospyros Kaki* as well as the blank of Comparative Example 2 were placed respectively in each of boxes having each a capacity of 10 liters, a hydrogen sulfide gas of an initial concentration of 5 ppm was flowed into the boxes, and they were left to stand for one hour. Thereafter, the concentration of the hydrogen sulfide gas in the each box was measured and the results were given in Table IV below.

TABLE IV

| | |
|---|---|
| Deodorant containing deodorizing ingredients from *Forsythia Viridissima* | 0.4 ppm |
| Deodorant containing deodorizing ingredients from *Diospyros Kaki* | 0.9 ppm |
| Blank | 3.6 ppm |

50 g of each of four sorts of the deodorants of Example 2 of the present invention containing deodorizing ingredients effective to the nitrogen compound odor and extracted from *Tsuga Sieboldii, Nandina Domestica* and *Loropetalum Chinense* as well as the blank of the Comparative Example 2 were placed in respective boxes of a capacity of 10 liters, an ammonia gas of an initial concentration of 30 ppm was flowed into the boxes, and they were left to stand for one hour. Thereafter, the concentration of the ammonia gas in each box was measured and the results were given in Table V below.

TABLE V

| | |
|---|---|
| Deodorant containing deodorizing ingredients from *Tsuga Sieboldii* | 4 ppm |
| Deodorant containing deodorizing ingredients from *Ginkgo Biloba* | 3 ppm |
| Deodorant containing deodorizing ingredients from *Nandina Domestica* | 2 ppm |
| Deodorant containing deodorizing ingredients from *Loropetalum Chinense* | 5 ppm |
| Blank | 22 ppm |

From Tables IV and V, it will be appreciated that the deodorants of Example 2 according to the present invention have a much high deodorizing effect.

EXAMPLE 3

Leaves of *Paulownia Tomentosa, Fartugium Japonicum* and *Oxalis Corymbosa* were subjected to 5-hour hot-water extraction respectively with 100 g of water at 60° C., and the extracted compositions were adjusted to be 0.1 wt. %, to obtain three different deodorizing liquids. 5 parts of glycerin was added as a humectant to each of these deodorizing liquids, and three groups of bentonite carriers having an average particle diameter of 5 mm were impregnated respectively with each of the thus obtained deodorizing liquids. The amount of impregnated liquid was 1 g per 1 g of the bentonite carrier. The bentonite carriers impregnated with the respectively different deodorizing liquids were heated at 50° C. for 4 hours and dried. Then each 20 g of the bentonite carriers impregnated with the different three deodorizing liquids were separately wrapped with non-woven cloth to form three filters, which were combined into a filter assembly.

COMPARATIVE EXAMPLE 4

30 g of bentonite having of 5 mm but not impregnated with such deodorizing liquids as extracted from the plants used in Example 3 was wrapped with non-woven cloth to make a blank in the form of a filter.

The filter impregnated with the deodorizing liquid obtained from *Fartugium Japonicum* in the above Example 3 of the present invention and the blank of Comparative Example 4 were placed in known air cleaners, which cleaners were placed in acrylic boxes of a capacity of 1 m³ and then a hydrogen sulfide gas having an initial concentration of 30 ppm was flowed into each box. Next, the air cleaners were driven to operate and the concentration of the hydrogen sulfide gas within the each box was sequentially measured by means of a gas chromatography. The measured results are as shown in FIG. 3. The filter impregnated with the deodorizing liquid obtained from *Oxalis Corymbosa* in Example 3 and the blank obtained in Comparative Example 4 were placed in respective known air cleaners, the air cleaners were placed in respective acrylic boxes of a capacity of 1 m³ and then an ammonia gas having an initial concentration of 50 ppm was flowed into each box. Next, the air cleaners were driven and the concentration of the ammonia gas within each box was sequentially measured with the gas chromatography. The measured results are as shown in FIG. 4. As seen from FIGS. 3 and 4, it has been found that the deodorizing filter of the present invention realizes the deodorizing action effective to the sulfur or nitrogen compound odor.

It has been found that the deodorizing ingredients extracted from *Paulownia Tomentosa* in Example 3 show an excellent deodorizing action with respect to such acid compound odor as acetic acid odor, as a result of measurement in the same manner as that for the sulfur and nitrogen compound odors. It has been also found that the deodorizing ingredients extracted from *Paulownia Tomentosa* show favorable deodorizing effect with respect to the sulfur compound odor.

EXAMPLE 4

Each 10 g of particulate bentonite carriers impregnated respectively with each of three different deodorizing liquids prepared in the same manner as Example 3 were separately wrapped with non-woven cloth to form three different filters, and the filters were combined into a filter assembly.

The filter assembly obtained in Example 4 according to the present invention was placed in the known air cleaner, which cleaner was put in the acrylic box of a capacity of 1 m³, and hydrogen sulfide and ammonia gases each having an initial concentration of 50 ppm were flowed into the box. Then the air cleaner was driven and the concentration of the hydrogen sulfide and ammonia gases was measured. The measurement results are as in FIG. 5. On the other hand, a filter assembly of the blanks prepared in Comparative Example 4 was measured through the same procedure as that for the filter assembly of Example 4, giving such results as in FIG. 6. As will be clear from comparison between FIGS. 5 and 6, the filter assembly of the present invention performs an excellent deodorizing action simultaneously with respect to both of the sulfur and nitrogen compound odors. When a butyric acid gas having an initial concentration of 50 ppm was flowed into each box simultaneously with the above odor measurement, the filter assembly of the invention has of course exhibited a remarkable difference in the deodorizing action.

COMPARATIVE EXAMPLE 5

The three different deodorizing liquids obtained in the same manner as in Example 3 were merely mixed, particulate bentonite was impregnated with the mixture, and 30 g of such bentonite was wrapped with non-woven cloth to form a filter, as in Example 3.

The filter obtained in Comparative Example 5 was placed in the air cleaner and measured according to the same procedure as in the measurement of the filter assembly of Example 4, giving such results as in FIG. 7. From comparison of FIG. 7 with FIG. 5 of Example 4 of the present invention, it will be seen that the filter of Comparative Example 5 cannot perform a sufficient deodorizing action.

EXAMPLE 5

Leaves of *Paulownia Tomentosa, Syringa Vulgaris, Osmanthus Fortuneiu, Fortugium Japonicum, Petasites Japonicus, Quercus Serrata, Pinus Thunbergii, Houttuynia Cordata* and *Oxalis Corniculata,* as well as a solvent of a mixture of water and ethanol at a ratio of 9 to 1, were put in the Soxhlet extractor to extract different deodorizing liquids. Among these deodorizing liquids, the ones extracted from *Paulownia Tomentosa, Syringa Vulgaris* and *Osmanthus Fortuneiu* and effective to sulfur compound odor were mixed together, whereas the ones extracted from *Pinus Thunbergii, Houttuynia Cordata* and *Oxalis Corniculata* and effective to nitrogen compound odor were mixed together. Each of these two mixtures was employed for the impregnation of each of polyurethane foam sheets to which active carbon was added, and the impregnated sheets were dried to form filters. In these filters, the amount of impregnated deodorizing liquids was 5 g per 1 g of polyurethane foam carrying the active carbon. Further, the filters impregnated with the mixture liquids for the different objective odors were stacked to form a filter assembly.

EXAMPLE 6

The deodorizing mixture liquids obtained in the same manner as in Example 5 of the present invention were used for impregnation also of the polyurethane foam sheets but having no active carbon added, the impregnated sheets were dried to form filters, and such filters impregnated with the mixture liquids for the different objective odors were stacked into a filter assembly.

COMPARATIVE EXAMPLE 6

Only polyurethane foam sheet not impregnated with any deodorizing liquids extracted from the plants in Example 5 and formed into a filter was used as a blank.

The filter assemblies obtained in the above Example 5 and 6 of the present invention as well as the blank of the Comparative Example 6 were installed in air cleaners, which cleaners were placed in acrylic boxes of a capacity of 1 m$^3$, and then ethyl mercaptan and trimethylamine gases respectively having an initial concentration of 50 ppm were flowed into the boxes. While operating the air cleaners, the concentration of the ethyl mercaptan and trimethylamine gases was, sequentially measured by a gas chromatography. The results as in FIGS. 8 to 10 were obtained from Examples 5 and 6 and Comparative Example 6, respectively. As seen from the drawings, the filter assemblies according to the present invention of FIGS. 8 and 9 have a remarkable deodorizing effect as compared with the blank of FIG. 10. It will also be appreciated that the filter assembly of FIG. 8 made of polyurethane foam carrying active carbon has a better deodorizing effect than that of FIG. 9 made of polyurethane foam carrying no active carbon.

In Examples 5 and 6, the deodorizing liquids effective to acid odor were extracted in the same quantities from *Quercus Serrata, Ligularia Tussilaginea* and *Petasites Japonicus* in the same manner for other plants, and were mixed together to prepare a filter similar to the other filters, and the prepared filter was inserted in the stack of the other filters to form a filter assembly. An acetic acid gas having an initial concentration of 50 ppm was flowed into the filter assembly, together with ethyl mercaptan and trimethylamine gases, and variation in the concentration of the acetic acid gas with time was measured. As a result, the similar remarkable deodorizing effect was observed. It has also been found that the Quercus, Fartugium and Patasites show a good deodorizing action with respect to the sulfur compound odor.

COMPARATIVE EXAMPLE 7

Only active carbon was added to the blank of Comparative Example 6 to form a filter.

Figure 9:
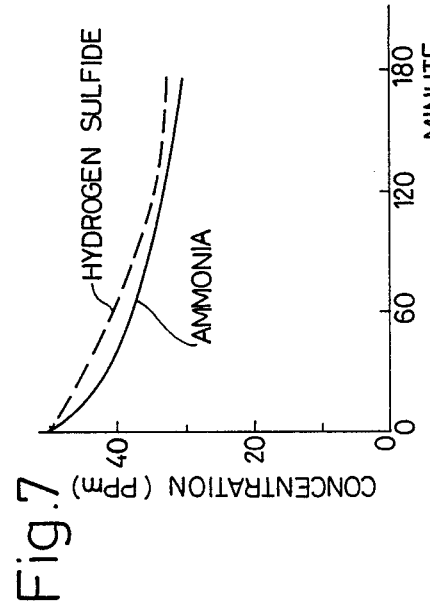
FIG. 9 is a graph showing variations in both of the trimethylamine and ethyl mercaptan concentrations with time due to still another filter assembly of the present invention.
Figure 8:
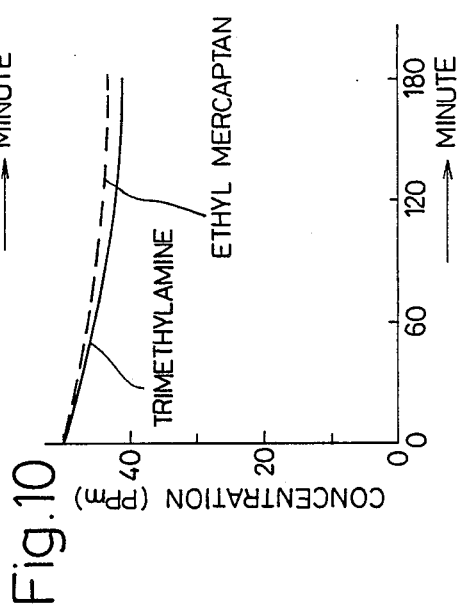
FIG. 8 is a graph showing variations in both of trimethylamine and ethyl mercaptan concentrations with time due to another filter assembly of the present invention.
Figure 10:
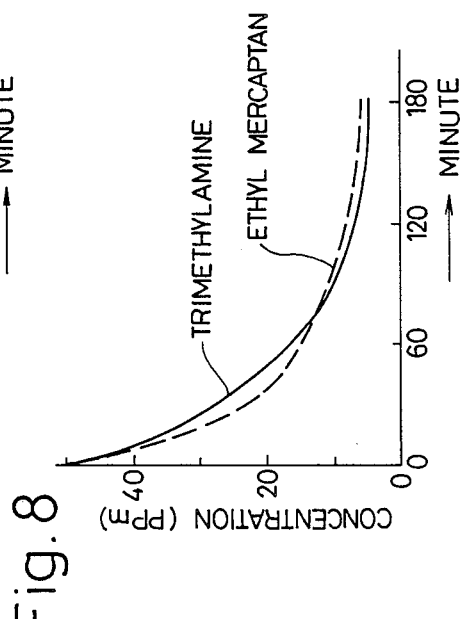
FIG. 10 is a graph showing variations in both the trimethylamine and ethyl mercaptan concentrations with time due to a blank corresponding to yet another filter assembly of the present invention.

The filter assembly of Example 5 and the filter of Comparative Example 7 were installed in air cleaners and subjected, once a day for continuous 10 days, to the same odor measurement as in the case of FIGS. 8 to 10. As a result, it has been found that the filter of Comparative Example 7 shows an insufficient deodorizing effect, and that this deodorizing effect has disappeared after 7 or 8 days, whereas the deodorizing effect of the filter assembly of Example 5 has shown no remarkable drop even after 10 days. This is considered to be because, in the filter assembly of Example 5, odor physically adsorbed into the active carbon is chemically decomposed by the chemical breakdown action of the deodorizing ingredient into carbon dioxide, nitrogen and so on which are hardly adsorbed into the active carbon, whereby the adsorption characteristic of the active carbon is restored and maintained in a state usable for long.

What is claimed as our invention is:

1. A deodorant consisting essentially of deodorizing ingredients extracted by hydrophilic organic solvents, water, or mixtures thereof from at least one plant selected from the group consisting of Osmanthus, Forsythia, Paulownia, Syringa, Diospyros, Quercus, Fartugium, Petasites, Pinus, Tsuga, Ginkgo, Nandina, Loropetalum, Houttuynia, and Oxalis, and a carrier impregnated with said deodorizing ingredients.

2. A deodorant according to claim 1, wherein said carrier is of a porous organic substance.

3. A deodorant according to claim 1, wherein said carrier is of a porous inorganic substance.

4. A deodorant according to claim 1, wherein said carrier is of one or more of inorganic substances selected from a group consisting of porous mineral, porous clay mineral and silica gel.

5. A deodorant according to claim 1, wherein said carrier is of a substance which is in gel state at normal temperature.

6. A deodorant consisting essentially of at least one deodorizing ingredient extracted by hydrophilic organic solvents, water, or mixtures thereof from at least one plant selected from the group consisting of Osmanthus, Forsythia, Paulownia, Syringa, Diospyros, Quercus, Fartugium, and Petasites and at least one deodorizing ingredient extracted by hydrophilic organic solvent, water, or mixtures thereof from at least one plant selected from the group consisting of Pinus, Tsuga, Ginkgo, Nandina, Loropetalum, Houttuyia and Oxalis, and at least one carrier impregnated with said deodorizing ingredients.

7. A deodorant according to claim 6, wherein said carriers are of one or more of inorganic substances selected from a group consisting of porous mineral, porous clay mineral and silica gel.

8. A deodorant according to claim 6, wherein said carriers are of a substance which is in gel state at normal temperature.

9. A deodorant consisting essentially of deodorizing ingredients extracted by hydrophilic organic solvents, water, or mixtures thereof from at least one plant selected from the group consisting of Osmanthus, Forsythia, Paulownia, Syringa, Diospyros, Quercus, Fartugium, Petasites, Ginkgo, Nandina, Loropetalum, Houttuynia, and Oxalis, and a carrier impregnated with said deodorizing ingredients.

10. A method of producing a deodorant, comprising the steps of extracting from a plant selected from the group consisting of Osmanthus, Forsythia, Paulownia, Syringa, Diopsypyros, Quercus, Fartugium, Petasites, Pinus, Tsuga, Ginkgo, Nandina, Loropetalum, Houttuynia, and Oxalis deodorizing ingredients effective with respect to sulfur and nitrogen compound odors with at least one solvent selected from the group consisting of hydrophilic organic solvents or water, adjusting of pH of a liquid containing said deodorizing ingredient so as to vary the pH level of said deodorizing ingredients effective with respect to said sulfur compound odor from neutral to weak basic and pH level of said deodorizing ingredients effective with respect to said nitrogen compound odor from acidic to weak acidic, impregnating at least one carrier with said deodorizing ingredients, and drying said impregnated carrier.

11. A method according to claim 10, wherein said extracting step is carried out in hot water.

12. The deodorant produced by the process of claim 10.

* * * * *